United States Patent [19]

Rhodes

[11] Patent Number: 5,508,310

[45] Date of Patent: Apr. 16, 1996

[54] IMMUNOPOTENTIATORY AGENTS AND PHYSIOLOGICALLY ACCEPTABLE SALTS THEREOF

[75] Inventor: John R. Rhodes, Beckenham, England

[73] Assignee: Burroughs Wellcome Co., Research Triangle Park, N.C.

[21] Appl. No.: 446,080

[22] Filed: May 19, 1995

Related U.S. Application Data

[63] Continuation of Ser. No. 112,992, Aug. 26, 1993, abandoned.

[30] Foreign Application Priority Data

| Oct. 1, 1992 | [GB] | United Kingdom | 9220715 |
| Dec. 23, 1992 | [GB] | United Kingdom | 9226874 |

[51] Int. Cl.$^6$ .......................... A61K 31/185; A61K 31/11
[52] U.S. Cl. .......................... 514/576; 514/699; 514/731; 514/855
[58] Field of Search .......................... 514/576, 699, 514/731, 885

[56] References Cited

U.S. PATENT DOCUMENTS 4,535,183   8/1985   Kneen ..................................... 514/568

FOREIGN PATENT DOCUMENTS

| 0054924A2 | 6/1982 | European Pat. Off. . |
| 0173262A2 | 3/1986 | European Pat. Off. . |
| 0217041A1 | 4/1987 | European Pat. Off. . |
| 0499015A1 | 8/1992 | European Pat. Off. . |
| 3508875 | 11/1985 | Germany . |
| WO92/03164 | 3/1992 | WIPO . |

OTHER PUBLICATIONS

Translation of European application Publication No. 0 217 041 A; Apr. 8, 1987; 6 pages.
Radiotherapy & Oncology vol. 16 1989 235–243 Elsevier.
Helv. Chim. Acta 19 1095–1107 (1936).
J. of Immunology vo. 139 2845–2849 Nov. 1, 1987.
J. of Immunology vol. 143 1482–1489 No. 5. Sep.
J. Lab Cln. Med. vol. 99 Nov. 4 526–532.
J. Exp. Med. Vol. 162 Sep. 1985 1060–1074.
European Search Report: International Application No. PCT/GB93/02039: Date of mailing Mar. 29, 1994: International filing date Sep. 30, 1993.
I. J. Radiation Oncology Biol. Phys. vol. 16, pp. 1179–1182: May 1989: No. 5.: G. E. Adams, D. Sc. et al., Induction of Severe Tumor Hyupoxia by Modifiers of The Oxygen Affinity of Hemoglobin.

*Primary Examiner*—Nathan M. Nutter
*Attorney, Agent, or Firm*—Donald Brown

[57] ABSTRACT

This invention relates to the use of a class of compounds as immunopotentiaters, compositions containing such compounds and their manufacture, combinations of such compounds with anti-tumor or anti-infective drugs and the use of such combinations in the prophylaxis or treatment of such diseases arising from tumors or infections.

6 Claims, 7 Drawing Sheets

IMMUNOPOTENTIATORY AGENTS AND PHYSIOLOGICALLY ACCEPTABLE SALTS THEREOF

This is a continuation of application Ser. No. 08/112,992 filed on Aug. 26, 1993 now abandoned.

This invention relates to the use of a class of compounds as immunopotentiaters, compositions containing such compounds and their manufacture, combinations of such compounds with anti-tumour or anti-infective drugs and the use of such combinations in the prophylaxis or treatment of such diseases arising from tumours or infections.

The principal protective function of the immune system relates to resistance to invasion by pathogens, including viruses, rickettsia, mycoplasma, bacteria, fungi and parasites of all types. Thus, improvement of immune response, particularly when depressed, enhances resistance to infection or infestation by any of the above pathogens.

A second protective function of the immune system is to resist engravement of foreign tissue, either natural or in a foetal-maternal relationship; or unnatural as performed by the transplant physician.

A further protective function of the immune system is thought to be resistance to malignant cell development as in cancer. Immunopotentiators are used in cancer to enhance tumour rejection and to inhibit tumour recurrences following other forms of therapy.

Yet another protective function involves maintaining non-reactivity to self by positive suppressor mechanisms. In auto-immune and related disorders, immune reactivity, directed at self-antigens or exaggerated, elevated responses, are apparent and self destructive.

Each of the protective functions of the immune system can be modified by nonspecific therapy with immunopotentiators alone or in combination with other agents employed to improve resistance to or to kill the invading pathogen. In addition, specific resistance can be augmented by use of immunopotentiators in conjunction with an antigen as in a vaccine employing, for example, a virus, tumour cells, etc. This use can be to induce either specific immunity or tolerance. The latter is exemplified by use with an antigen in allergy or an auto-immune disease. Use of immunopotentiators may be either therapeutic or prophylactic; the latter is used particularly in aging, where infection, auto-immunity, and cancer are more common. The timing and route of administration are critical in determining whether a positive or negative response results. Any agent capable of augmenting an immune response may inhibit it depending on timing and dose; thus, under certain circumstances an immunopotentiator could be used as an immunosuppressive agent for use in allergy, auto-immunity and transplantation.

By immunopotentiator is meant an agent which is capable of restoring a depressed immune function, or enhancing normal immune function, or both. However because of certain elements of the immune system an immunopotentiator can also have immunosuppressive effects.

Immune responses are orchestrated by T-lymphocytes whose stereo-specific receptors are triggered by antigenic fragments bound to specialised molecules (MHC) on the surface of antigen presenting cells. In addition to the specific interaction between T-cell receptor and antigen-MHC complex, T-cells require costimulatory signals which are provided by antigen presenting cells. The interaction between antigen presenting cells and T-cells involves accessory adhesion molecules some of which are linked to the T-cell receptor:antigen-MHC interaction and others which are separate from this interaction. Some of these adhesion molecules provide costimulatory signals. In addition, studies made in vitro have established that transient covalent chemical reactions between cell surface ligands are essential in the antigen-specific activation of T-cells (Rhodes, J., (1989), J. Immunol. 143:1482; Gao, X. M. & Rhodes, J. (1990), J. Immunol. 144:2883; Rhodes, J. (1990), J. Immunol. 145:463). These take the form of carbonyl-amino condensation (Schiff base formation) between groups on APC and T-cell surface.

The patent specification WO 9203164 discloses a novel adjuvant, NAGO, which works by enzymatically increasing the expression of Schiff base forming ligands. The patent specification DE 3508875 discloses cinnaldehyde as an immunopotentiator in rabbits infected with Herpes PSR virus. The patent specification U.S. Pat. No. 4,535,183 discloses certain compounds of this invention, their synthesis and their properties as "left-shifers" of the oxygen-dissociation curve. All references identified herein above are hereby incorporated by reference thereto.

Therapeutic targets for an immunopotentiatory drug include chronic virus infections such as viral hepatitis and human immunodeficiency virus. Cancer is also a therapeutic target. Evidence is accumulating to show that chronic virus infections and malignant tumours evade the immune system in various ways. Thus, although cytotoxic T-cells and antibodies are produced against abnormal cells (whether virus infected or malignant) the immune system fails to halt the pathogenic process. A common process of evasion may exist in which viruses and tumours exploit the mechanism by which non-responsiveness to self is maintained. Self-reactive T-cells are eliminated during foetal development by ligation of the T-cell receptor (TCR) in the absence of costimulatory signals. As a result such T-cells undergo programmed cell death. Self-reactive T-cells in the periphery are also maintained in a non-responsive state through ligation of the TCR in the absence or costimulation. This is termed anergy. Evasion of the immune system may occur in pathogenic processes when costimulatory signals are subverted. The result is that T-cells responding to the disease become anergic or undergo programmed cell death. There is increasing evidence for the latter in AIDS. Schiff base-forming immunopotentiators should be effective in preventing this escape mechanism because they act by providing costimulation to T-cells. In this way Schiff base-forming immunopotentiatory drugs may expressly correct the lesion in immunity that allows viral infections to persist and certain malignant tumours to progress.

SUMMARY

It has now been found that certain small molecules that participate in carbonyl-amino condensation reactions, surprisingly act as immunopotentiators.

The present invention relates to the use of compounds or physiologically acceptable salts thereof, which form Schiff bases or hydrazones with T-cell surface carbonyl or amino groups, with the proviso that the compounds cinnaldehyde, 4-(2-formyl-3-hydroxyphenoxymethyl)benzoic acid and physiologically acceptable salts thereof are excluded, for the manufacture of a medicament for the potentiation of an immune response.

The present invention more particularly relates to the use of a compound of the formula (I):

$$B^1-N \tag{I}$$

or a physiologically acceptable salt thereof, for the manufacture of a medicament for the potentiation of an immune response, wherein wherein N is hydrogen or n is 0 or 1;

B is hydrogen or $C_{1-4}$ alkyl;

$B^1$ is hydrogen or an optionally substituted phenyl when $B^1$ is an optionally substituted phenyl the substituents are defined as $Y^1, Y^2, Y^3, Y^4, Y^5$ and $Y^6$ as defined below in formula (II).

$B^2$ is methyl or may be linked to $B^1$ when $B^1$ is phenyl to form a optionally substituted bicyclic ring system containing 8 or 10 atoms of which one may be oxygen and the rest carbon, or when n is 1, $B^1$ is hydrogen and $B^2$ is $CH_2CO(CH_2)_xCOOH$ wherein x is 1 to 7.

The preferred group of compounds of formula (I) wherein N is hydrogen and $B^1$ is represented by formula (II):

In formula (II) as set forth above, $Y^1$ is selected from hydrogen, hydroxy, $C_{1-4}$ alkylamino, and alkanoylamino having 1 to 4 carbon atoms in the alkyl moiety thereof, $Y^2, Y^3$ and $Y^4$ are independently selected from hydrogen, halogen, $C_{1-4}$ alkyl, $C_{1-4}$ alkoxy, trifluoromethyl, hydroxyl and benzyloxy; and $Y^5$ is hydroxyl or a group $Q^1$ wherein $Q^1$ is either where $Q^2$ and $Q^3$ are independently selected from hydrogen and $C_{1-4}$ alkyl;

X is selected from cyano, carboxyl or and functional derivative thereof, 5-tetrazolyl and alkylsulphonylcarbamoyl having 1 to 6 carbon atoms in the alkyl moiety thereof; and n is 0 to 6.

$Y^6$ is $—(C_pH_{2p})CHO$, wherein p=0 to 5 when n is >1 the formyl(—CHO) group may be on any carbon atom and the alkylene ($C_nH_2n$) may be linear or branched;

or $Y^6$ is $(CH_2CO)_q—X^1$ or $(COCH_2)q—X^1$ where q=1 to 3 and $X^1$ is methoxyphenyl, or $C_{1-4}$ alkyl and physiologically acceptable salts thereof.

As a subclass within formula (I) may be mentioned the use of compounds wherein

X is selected from cyano, 5-tetrazolyl, alkylsulphonylcarbamoyl having 1 to 6 carbon atoms in the alkyl moiety thereof and a group —CO.Y, where Y is $—OR^1$ and $R^1$ is hydrogen, alkyl of 1 to 4 carbon atoms or benzyl, or Y is $—NR^2R^3$ where $R^2$ and $R^3$ are independently hydrogen or alkyl of 1 to 4 carbon atoms, Compounds within formula (I) without the proviso wherein X is a carboxyl derivative include:

esters, including aliphatic and aromatic hydrocarbon esters such as alkyl and aralkyl esters where for example the alkyl has 1 to 12 and preferably 1 to 4 carbon atoms (in particular methyl, ethyl, isopropyl and t-butyl) and where the aralkyl is for example benzyl and amino acid esters (for example, L-valyl or L-isoleucyl); and amides, including the unsubstituted amide, N-substituted amides and N,N-disubstituted amides (embracing cyclic and heterocyclic amides) where the substituent group(s) is (are) for example aliphatic hydrocarbon such as alkyl, in particular alkyl of 1 to 4 carbon atoms such as methyl, ethyl, isopropyl and t-butyl.

Compounds of formula (II) with the proviso wherein $Y^1$ is alkylamino can form acid addition salts; in such salts the identity of the acid is of less importance although for use in medicine it is physiologically acceptable to the recipient. Suitable acids are well known in the art, for example hydrochloric acid and acetic acid.

As a subclass within formula (I) may be mentioned the use of compounds wherein $B_1$ and $B_2$ form a bicyclic ring system, the bicyclic ring system is selected from coumarin, tetralone, benzofuranone or naphthoquinone substituted by up to four substituents selected from hydrogen, $C_{1-4}$ alkoxy, hydroxy or hydroxy substituted phenyl together with physiologically acceptable salts thereof.

Therefore, a compound of the invention and physiologically acceptable salts thereof, may be used for the treatment of diseases where there is a defect in the immune system and/or an ineffective host defence mechanism, or to enhance activity of the immune system above normal levels.

In a further aspect, a compound of formula (I) and physiologically acceptable salts thereof, may be used for the treatment of diseases where there is a defect in the immune system and/or an ineffective host defence mechanism, or to enhance activity to the immune system above normal levels.

A compound of the invention and physiologically acceptable salts thereof may administered for the treatment or prophylaxis of immunodeficient mammals alone or combination with other therapeutic agents, for example, with other antiviral agents, with other anticancer agents.

A compound of formula (I) and physiologically acceptable salts thereof may be administered for the treatment or prophylaxis of immunodeficient mammals alone or in combination with other therapeutic agents, for example, with other antiviral agents, or with other anticancer agents.

DETAILED DESCRIPTION OF THE INVENTION

By potentiation of an immune response is meant restoration of a depressed immune function, enhancement of a normal immune function, or both. Immune function is defined as the development and expression of humoral (antibody-mediated) immunity, cellular (T-cell-mediated) immunity, or macrophage and granulocyte mediated resistance.

In this specification the term "immunodeficient patient" will be used to describe patients with a deficient or defective immune system. An immunodeficient patient can be characterised by means of a T-lymphocyte proliferation assay. Using this assay immunodeficient patients are characterised by a reduced ability of the T-cells to respond to stimulation by mitogens. An example of a mitogen commonly used in this assay is phytohaemagglutinin (PHA).

Immunodeficiency and immunosuppression is thought to occur in many clinical situations where there are lesions in signalling to lymphocytes, particularly T-cells which orchestrate the immune response. T-cells require two signals in order to initiate an effective immune response and these are:

(i) occupation of the specific T-cell receptor for antigen, and (ii) stimulation through costimulatory receptors.

In the absence of signal (ii), not only do T-cells fail to respond but they may also become chronically paralysed or anergic. Persistent viral and bacterial infections and neoplastic disease can produce T-cell hyporeponsiveness by interfering in various ways with the delivery of second signals and in this way evade the immune response. The compound of formula (I) appears to work by substituting or otherwise compensating for deficient costimulatory signals to T-cells.

There is a variety of circumstances in which the immune system may be defective or deficient. Thus, for example immune system deficiency is common in immature or premature infants (neonates). It may also result from suppression by certain drugs, which may be deliberate e.g. as a side-effect of cancer chemotherapy. Disordered growth of one or more constituent parts of the immune system, e.g. as in certain forms of cancer, may also result in immunodeficiency. Immune deficiency may furthermore be caused by viral infections, including human immunodeficiency virus (HIV).

By an "effective amount" is meant the amount of a compound of formula (I) which will restore immune function to normal levels, or increase immune function above normal levels in order to eliminate infection.

A further aspect of the present invention provides a method of treating immunodeficient patients, which comprises administering to a mammal (including human) an effective amount of a compound of formula (I), or a physiologically acceptable salt thereof.

According to a further aspect of the present invention provides for the use of a compound of formula I or physiologically acceptable salts thereof for the treatment and/or prophylaxis of acute and chronic vital infections.

Examples of acute viruses against which immunopotentiatory therapy with a compound of formula I or physiologically acceptable salts thereof may be used, preferably in conjunction with an antiviral agent, are:

herpes viruses, influenza viruses, parainfluenza viruses, adenoviruses, coxsakie viruses, picorna viruses, rotaviruses, heptatitis A virus, mumps virus, rubella virus, measles virus, pox viruses, respiratory syncytial viruses, papilloma viruses, and enteroviruses, arenavirus, rhinoviruses, poliovirus, Newcastle disease virus, rabies virus, arboviruses.

Examples of chronic vital infections against which immunopotentiatory therapy with a compound of formula I or physiologically acceptable salts thereof may be used are persistent herpes virus infections, Epstein Ban virus infection, persistent rubella infections, papovirus infections, hepatitis virus infections and human immunodeficiency virus infection.

The present invention is applicable to the treatment of viral hepatitis in all of its forms, five types now being recognised hepatitis A, B, C, D and E respectively.

Of the DNA viruses, those of the herpes group are the sources of the most common viral illnesses in man. The group includes herpes simplex virus (HSV), varicella zoster virus (VZV), cytomegalovirus (CMV); Epstein-Barr virus (EBV) and human herpes virus 6 (HHV6). HSV 1 and HSV 2 are some of the most common infectious agents of man. Most of these viruses are able to persist in the host's neural cells; once infected, individuals are at risk of recurrent clinical manifestations of infection which can be both physically and psychologically distressing.

HSV infection is often characterised by extensive and debilitating lesions of the skin, mouth and/or genitals. Primary infections may be subclinical although tend to be more severe than infections in individuals previously exposed to the virus. Ocular infection by HSV can lead to keratitis or cataracts thereby endangering the host's sight. Infection in the newborn, in immunocompromised patients including AIDS patients or penetration of the infection into the central nervous system, can prove fatal.

Transmission of the virus is by direct physical contact between a host and a recipient; the spread of HSV infection is therefore considered a very significant social problem, particularly as no effective vaccine is yet available.

Varicella zoster (VZV) is a herpesvirus which causes chickenpox and shingles. Chickenpox is the primary disease produced in a host without immunity and in young children is usually a mild illness characterised by a vesicular rash and fever. Shingles or zoster is the recurrent form of the disease which occurs in adults who were previously infected with varicella-zoster virus. The clinical manifestations of shingles are characterised by neuralgia and a vescicular skin rash that is unilateral and dermatomal in distribution. Spread of inflammation may lead to paralysis or convulsions. Coma can occur if the meninges becomes affected. In immunodeficient patients VZV may disseminate causing serious or even fatal illness. VZV is of serious concern in patients receiving immunosuppressive drugs for transplant purposes or for treatment of malignant neoplasia and is a serious complication of AIDS patients due to their impaired immune system.

In common with other herpes viruses, infection with CMV leads to a lifelong association of virus and host and, following a primary infection, virus may be shed for a number of years. Congenital infection following infection of the mother during pregnancy may give rise to clinical effects such as death or gross disease (microcephaly, hepatosplenomegaly, jaundice, mental retardation), retinitis leading to blindness or, in less severe forms, failure to thrive, and susceptibility to chest and ear infections. CMV infection in patients who are immunocompromised for example as a result of malignancy, treatment with immunosuppressive drugs following transplantation or infection with Human Immunodeficiency virus may give rise to retinitis, pneumoitis, gastrointestinal disorders and neurological diseases. CMV infection in AIDS patients is a predominant cause or morbidity as, in 50–80% of the adult population, it is present in a latent form and can be re-activated in immunocompromised patients.

Epstein-Barr virus (EBV) causes infectious mononucleosis and hairy leukoplakis, and is also suggested as the causative agent of human cancer, such as nasopharyngeal cancer, immunoblastic lymphoma, Burkitt's lymphoma.

HBV is a vital pathogen of world-wide major importance. The virus is aetiologically associated with primary hepatocellular carcinoma and is thought to cause 80% of the world's liver cancer. In the United States more than ten thousand people are hospitalised for HBV illness each year, and an average of 250 die with fulminant disease. The United States currently contains an estimated pool of 500,000–1-million infectious carriers. Chronic active hepatitis generally develops in over 25% of carriers, and often progresses to cirrhosis. Clinical effects of infection with HBV range from headache, fever, malaise, nausea, vomiting, anorexia and abdominal pains. Replication of the virus is usually controlled by the immune response, with a course of recovery lasting weeks or months in humans, but infection may be more severe leading to persistent chronic liver disease outlined above.

Of the RNA viruses, one group has assumed a particular importance this is the retroviruses. Retroviruses form a sub-group of RNA viruses which, in order to replicate, must first 'reverse transcribe' the RNA of their genome into DNA ('transcription' conventionally describes the synthesis of RNA from DNA). Once in the form of DNA, the vital genome may be incorporated into the host cell genome, allowing it to take advantage of the host cell's transcription/translation machinery for the purposes of replication. Once incorporated, the viral DNA is virtually indistinguishable from the host's DNA and, in this state, the virus may persist for the life of the cell.

In the case of immunosuppression resulting from HIV infection, prophylaxis may be required by those diagnosed as seropositive for HIV i.e. having antibodies to HIV, and those with PGL (progressive generalised lymphadenopathy) or ARC (AIDS-related complex) as well as patients suffering from AIDS or patients suffering from AIDS-like immune deficiencies where the HIV infection is not detectable and who also require immunorestoration by means that are not specific to any particular virus.

The compounds according to the invention may be employed alone or in combination with other therapeutic agents for the treatment of the above infections or conditions. Combination therapies according to the present invention comprise, the administration of at least one compound of the formula (I) or a physiologically functional derivative thereof and at least one other pharmaceutically active ingredient. The active ingredient(s) and pharmacologically active agents may be administered together or separately and, when administered separately this may occur simultaneously or sequentially in any order. The amounts of the active ingredient(s) and pharmacologically active agents(s) and the relative timings of administration will be selected in order to achieve the desired combined therapeutic effect. Preferably the combination therapy involves the administration of one compound of the formula (I) or a physiologically functional derivative thereof and one of the agents mentioned herein below.

Examples of such further therapeutic agents include agents that are effective for the treatment of HIV infections or associated conditions such as 3'-azido-3'-deoxythymidine (zidovudine), other 2',3'-dideoxynucleosides such as 2',3'-didoxycytidine, 2',3'-dideoxyadenosine and 2',3'-didoxyinosine, carbovir, acyclic nucleosides (for example, acyclovir), 2',3'-didehydrothymidine, protease inhibitors such as N-tert-butyl-dechydro-2-[-2(R)-hydroxy-4-phenyl-3(S)-[ [N-2-quinolyl-carbonyl)-L-asparginyl]butyl]-(4aS,8aS)-isoquinoline-3(S)-carboxamide (Ro31-8959), oxathiolan nucleoside analogues such as cis-1-(2-hydroxymethyl)-1,3-oxathiolan-5-yl)-cytosine or cis-1-(2-(hydroxymethyl)-1,3-oxathiolan-5-yl)-5-fluoro-cytosine, 3'-deoxy-3'-fluorothymidine, 2',3'-dideoxy-5-ethynyl-3'-fluorouridine, 5-chloro-2',3'-dideoxy-3'fluorouridine, Ribavirin, 9-[4-hydroxy-2-(hydroxymethyl)but-1-yl]guanine (H2G), TAT inhibitors such as 7-chloro-5-(2-pyrryl)-3H-1,4-benzodiazepin-2(H)-one (Ro5-3335), or 7-chloro-1,3-dihydro-5-(1H-pyrrol-2-yl)-3H-1,4-benzodiazepin-2-amine (Ro24-7429) interferons such as α-interferon, renal excretion inhibitors such as probenecid, nucleoside transport inhibitors such as dipyridamole; pentoxifylline, NAcetylCysteine, Procysteine, α-trichosanthin, phosphonoformic acid, as well as immunodulators such as interleukin II, granulocyte macrophage colony stimulating factors, erythropoetin, soluble CD$_4$ and genetically engineered derivatives thereof. Examples of such further therapeutic agents which are effective for the treatment of HBV infections include carbovir, oxathiolan nucleoside analogues such as cis-1-(2-hydroxymethyl)-1,3-oxathiolan-5-yl)-cytosine or cis-1-(2-(hydroxymethyl)-1,3-oxathiolan-5-yl-5-fluoro-cytosine, 2',3'-didoxy-5-ethynyl-3'-fluorouridine, 5-chloro-2',3'-didoxy-3'-fluorouridine, 1-(β-D-arabinofuranosyl)-5-propynyluracil, acyclovir and interferons, such as α interferon.

It has been reported (Hughes, W. T. (1987) Treatment and Prophylaxis of *Pneumocystis carinii* pneumonia, Parasitology Today 3(11) 332–335) that at least 60% of patients with acquired immunodeficiency syndrome (AIDS) suffer from *Pneumocystis carinii* pneumonia.

Without treatment, *Pneumocystis carinii* pneumonia is almost always fatal in immunocompromised hosts. The most widely used treatments for this condition are trimethoprim-sulphamethoxaole (cotrimoxaole) and pentamidine. However, both of these treatments have been reported to be only around 50–70% effective in AIDS patients and to produce a much higher than usual incidence of adverse reactions (about 50%) (Wofsy, C. B. Antimicrobial Agents Annual, 1986, Vol 1, p377–400). There is thus a need for new agents, especially for the prophylaxis of *P. carinii* pneumonia.

In another aspect the present invention provides the use of a compound of formula (12) and physiologically acceptable salts thereof for the manufacture of a medicament for the treatment and/or prophylaxis of *Pneumocystis carinii* infections in mammals (including humans).

In a yet further aspect the present invention provides for the use of a compound of formula (I) and physiologically acceptable salts thereof to treat conditions resulting from relative T-cell deficiencies such as DiGeorge Syndrome, fungal infections, mycoplasma infections, tuberculosis, leprosy, and systemic lupus erythemotosus.

In another aspect of the present invention provides for the use of the compound of formula (I) and physiologically acceptable salts thereof for the manufacture of a medicament for the treatment and/or prophylaxis of cancer in mammals (including humans).

In a further aspect of the present invention provides for the use of the compound of formula (I) and physiologically acceptable salts thereof for the manufacture of a medicament for the treatment and/or prophylaxis of cancer other than in radiotherapy.

Compounds of formula (I) or physiologically acceptable salts thereof can also be used for the treatment and prophylaxis of cancer at a dosage substantially lower than the dosage used previously disclosed in U.S. Pat. No. 4,535,183.

Examples of forms of cancers particularly suitable for treatment with the compound of formula I are: melanoma, breast cancer, colon cancer, cancer of the head and neck, gastric cancer, renal cancer, laryngeal cancer, rectal cancer, and non-Hodgkins lymphoma. Cancers that express turnout specific antigens or antigens rarely expressed or expressed at very low density on normal cells, are likely therapeutic targets. Cancers which contain turnout specific cytotoxic T-cells which are anergic or otherwise ineffective are likely targets for therapy. Surgically resetted tumours where there is a high risk of recurrence are also suitable for therapy with the compound of formula (I).

Compounds of formula (I) are thought to act by providing a co-stimulatory signal to cloned (partially) activated T-cells in vitro, thus maximally activating T-cells.

A further aspect of the present invention provides for the use, as a vaccine adjuvant, of a compound of formula (I) or physiologically acceptable salts. A vaccine may therefore be prepared by formulating the antigenic component with the compound of formula (I).

Compounds of formula (I) may be administered to the human recipient by a route selected from oral, parenteral (including subcutaneous, intradermal, intramuscular and intravenous), rectal and inhalation. The size of an effective dose of a compound will depend upon a number of factors including the identity of the recipient, the type of immunopotentiation involved, the severity of the condition to be treated and the route of administration, and will ultimately be at the discretion of the attendant physician.

For each of the aforementioned conditions, such an effective dose will generally be in the range 0.5 to 50 mg/kg bodyweight of human recipient per day, preferably in the range 0.1 to 20 mg/kg bodyweight per day and most preferably in the range 1 to 10 mg/kg bodyweight per day; an optimum dose is 3 mg/kg bodyweight per day. The above doses are for human usage.

The desired dose may be presented as between two and four sub-doses administered at appropriate intervals throughout the day. Thus where three sub-doses are employed each will generally lie in the range 0.03 mg to 33 mg, preferably 0.16 mg to 166 mg and most preferably 0.3 to 6.6 mg (acid)/kg bodyweight with an optimum of 1.0 mg (acid)/kg bodyweight. A daily dose for a human weighing of the order of 50 kg will thus generally lie in the range 5 mg to 5 g (acid), preferably in the range 25 mg to 2.5 g (acid) and most preferably in the range 50 mg to 1 g (acid). Optimally a human daily dose is 150 mg (acid). The desired dose is preferably presented as a daily dose over a period of 28 days.

While it is possible for the compounds of formula (I) to be administered as the raw chemical it is preferable to present them as a pharmaceutical formulation preparation. The formulations of the present invention comprise a compound of formula (I), as above defined, together with one or more acceptable carriers therefor and optionally other therapeutic ingredients. The carrier(s) must be 'acceptable' in the sense of being compatible with the other ingredients of the formulation and not deleterious to the recipient thereof.

The formulations include those suitable for oral, parenteral (including subcutaneous, intradermal, intramuscular and intravenous) and rectal administration although the most suitable route may depend upon tier example the condition of the recipient. The formulations may conveniently be presented in unit dosage form and may be prepared by any of the methods well known in the art of pharmacy. All methods include the step of bringing into association the compound of formula (I) (the active ingredient) with the carder which constitutes one or more accessory ingredients. In general the formulations are prepared by uniformly and intimately bringing into association the active ingredient with liquid carriers or finely divided solid carders or both, and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression, or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Formulations for rectal administration may be presented as a suppository with the usual carriers such as cocoa butter.

U.S. Pat. No. 4,535,183 contains no invitation to administer the compound of formula (Ia) by the nasal or pulmonary route nor any suggestion that the said compound, if 
administered in such a manner, would be effective in the treatment of the conditions therein taught; the said disclosure likewise contains no description of any formulation suitable for administration by the nasal or pulmonary route.

Formulations suitable for pulmonary administration via the buccal cavity are presented such that particles containing the active ingredient and desirably having a diameter in the range 0.5 to 7 microns are delivered into the bronchial tree of the recipient.

As one possibility such formulations are in the form of finely comminuted powders which may conveniently be presented either in a pierceable capsule, suitably of for example gelatin, for use in an inhalation device, or alternatively as a self-propelling formulation comprising active ingredient, a suitable liquid propellant and optionally other ingredients such as surfactant and/or a solid diluent. Self-propelling formulations may also be employed wherein the active ingredient is dispensed in the form of droplets of a solution or suspension.

Such self-propelling formulations are analogous to those known in the art and may be prepared by established procedures. Suitable they are presented in a container provided with either a mannually-operable or automatically functioning valve having the desired spray characteristics; advantageously the valve is of a metered type delivering a fixed volume, for example 50 to 100 microliters, upon each operation thereof.

As a further possibility the active ingredient may be in the form of a solution for use in an atomiser or nebuliser whereby an accelerated airstream or ultrasonic agitation is employed to produce a fine droplet mist for inhalation.

Formulations suitable for nasal administration include presentations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of the active ingredient in aqueous or oily solution.

Preferred unit dosage formulations are those containing an effective dose, hereinabove recited, or an appropriate fraction thereof, of the active ingredient.

The following Examples are provided in illustration of the present invention and should not be construed as in any way constituting a limitation thereof. All temperatures are in degrees Celsius (°C.).

Pharmaceutical Formulations

| Solution for nebulisation | | |
|---|---|---|
| Compound of formula (I) | | 1.0 mg |
| Water for injections | to | 10.0 mL |

Dissolve the compound of formula (I) as for injections. Sterilize the solution by passage through a membrane filter, 0.2 μm pore size, collecting the filtrate in a sterile receiver. Fill into sterile glass ampoules, 10 mL/ampoule, under aseptic conditions and seal each ampoule by fusion of the glass.

| Self-propelling formulation | | |
|---|---|---|
| Compound of formula (I), micronised | | 1.0 mg |
| Propellant | to | 5.0 mL |

Suspend the micronised compound of formula (I) in the propellant. Fill this suspension under pressure into preformed, valved aerosol canisters, 5 mL/canister, through the valve orifice.

The propellant is a commercially available mixture of trichloromonofluoromethane, dichlorodifluoromethane and dichlorotetrafluoroethane.

| Powder for inhalation | |
|---|---|
| Compound of formula (I), micronised | 1.0 mg |
| Lactose | 29.0 mg |

Triturate and blend the micronised compound of formula (I) with the lactose. Fill the resulting powder blend into hard gelatin capsule shells, 30 mg per capsule. Alternatively, the micronised compound of formula (I) could be compressed into a plug and a device which delivers small amounts of the compound of formula (I) into the airstream can be used.

| Nasal drops | | |
|---|---|---|
| Compound of formula (I) | | 100 mg |
| Methyl p-hydroxybenzoate | | 10 mg |
| Water for injections | to | 10 mL |

Dissolve the compound of formula (I) and the methyl p-hydroxybenzoate in the water for injections. Fill this solution into suitable dropper bottles, 10 mL/bottle, and close by securing the dropper nozzle and bottle cap.

| Tablet | |
|---|---|
| Compound of formula (1) | 100 mg |
| Lactose | 100 mg |
| Starch | 50 mg |
| Polyvinylpyrrolidone | 5 mg |
| Magnesium Stearate | 5 mg |
| | 260 mg |

The Compound, Lactose and Starch are mixed together and then granulated with a solution of Polyvinyl-pyrrolidone in water. After drying the granules, the Magnesium Stearate is mixed in and tablets compressed at an average weight of 260 mg.

| Capsule | |
|---|---|
| Compound of formula (I) | 100 mg |
| Dibasic Calcium Phosphate Dihydrate | 100 mg |
| Sodium Starch Glycolate | 16 mg |
| Methylcellulose 400 cps | 5 mg |
| Stearic Acid | 4 mg |
| Talc | 5 mg |
| | 230 mg |

The compound, dibasic calcium phosphate, dihydrate and sodium starch glycolate are mixed together and then granulated with a solution of the Methylcellulose in water. After drying, the granules are mixed with the Stearic Acid and Talc and the mixture filled into gelatin capsules at an average fill weight of 230 mg.

| Suppository | |
|---|---|
| Compound of formula (I) | 100 mg |
| Suppository Base (Mixed | 1700 mg |
| Glycerides of saturated fatty acids) | |
| | 1800 mg |

Grind the Compound to a particle size below 150μ. Add the suppository base at 38°–40° C. Mix to give a uniform dispersion. Pour into suppository moulds and allow to cool.

| Injection - Single dose, intravenous | |
|---|---|
| Compound of formula (I) | 100 mg |
| Sodium Hydroxide Solution (30%) | q.s. |
| Water for Injections to | 5 mL |

Suspend the Compound in some of the Water for Injections. Adjust the pH to 10 to 10.5 by addition of Sodium Hydroxide Solution. Add sufficient Water for Injections to produce the required final volume. Re-check the pH. Sterilise by passage through a sterile membrane filter of 0.22μ pore size. Fill under aseptic conditions into sterile vials and freeze dry.

| Injection - Multidose, intramuscular | |
|---|---|
| Compound of formula (I), sterile | 1000 mg |
| Polysorbate 20 | 3 mg |
| Polyvinylpyrrolidone | 1000 mg |
| Chlorocresol | 60 mg |
| Sodium Chloride | q.s. to isotonicity |
| Water for Injections to | 30 mL |

Dissolve the Polysorbate 20, Polyvinylpyrrolidone, Sodium Chloride and Chlorocresol in Water for Injections. Sterile filter, 0.22μ. Grind the sterile Compound to a particle size below 20μ and add to the filtered solution. Mix until a uniform dispersion is achieved. Fill into sterile glass vials.

| Prolonged Release Tablet | |
|---|---|
| Compound | 200 mg |
| Casein | 195 mg |
| Hydrogenated Castor Oil | 400 mg |
| Magnesium Stearate | 5 mg |
| | 800 mg |

Melt the Hydrogenated Castor Oil and add the Compound, ground to a particle size of less than 150μ. Add the Casein. Mix until uniform. Allow to cool and mill to a granule. Mix in the Magnesium Stearate and compress to an average weight of 1,200 mg.

In the foregoing the "Compound" refers to a compound of formula (I) as hereinbefore defined.

Preferred unit dosage formulations are those containing a daily dose or unit daily sub-dose, as hereinabove recited, or an appropriate fraction thereof, of a compound of formula (I) or physiologically acceptable salts thereof.

It should be understood that in addition to the ingredients particularly mentioned above the formulations of this invention may include other agents conventional in the art having regard to the type of formulation in question, for example those suitable for oral administration may include flavouring agents.

A compound of formula (I) or physiologically acceptable salts thereof may also be presented as depot formulations of the kind known in the art from which the active ingredient is released, over a prolonged period, once the formulation is in place within the body of the recipient.

The results of tests with a compound of formula (I) are described in the following experimental examples in order to illustrate the effect of the present invention in more detail:

EXAMPLE 1

Mice were injected subcutaneously in the dorsal mid-line either with antigen alone, with antigen plus a conventional adjuvant, or with antigen plus test compound. Subsequent additional injections of test compound were also given where specified for up to four days at the same injection site. After seven days regional (inguinal) lymph nodes were removed and the lymph node cells restimulated with antigen alone. Antigen specific proliferation of lymphocytes was measured after a further four days by a standard procedure employing $^3$H-thymidine uptake into DNA and liquid scintillation spectrometry. Tests for humoral immunity were performed by administering antigen and test compounds in the same way. After 1–2 weeks blood was sampled by venapuncture and serum antibody was assayed by an enzyme-linked immunosorbent (ELISA) assay.

RESULTS

Figure 1:
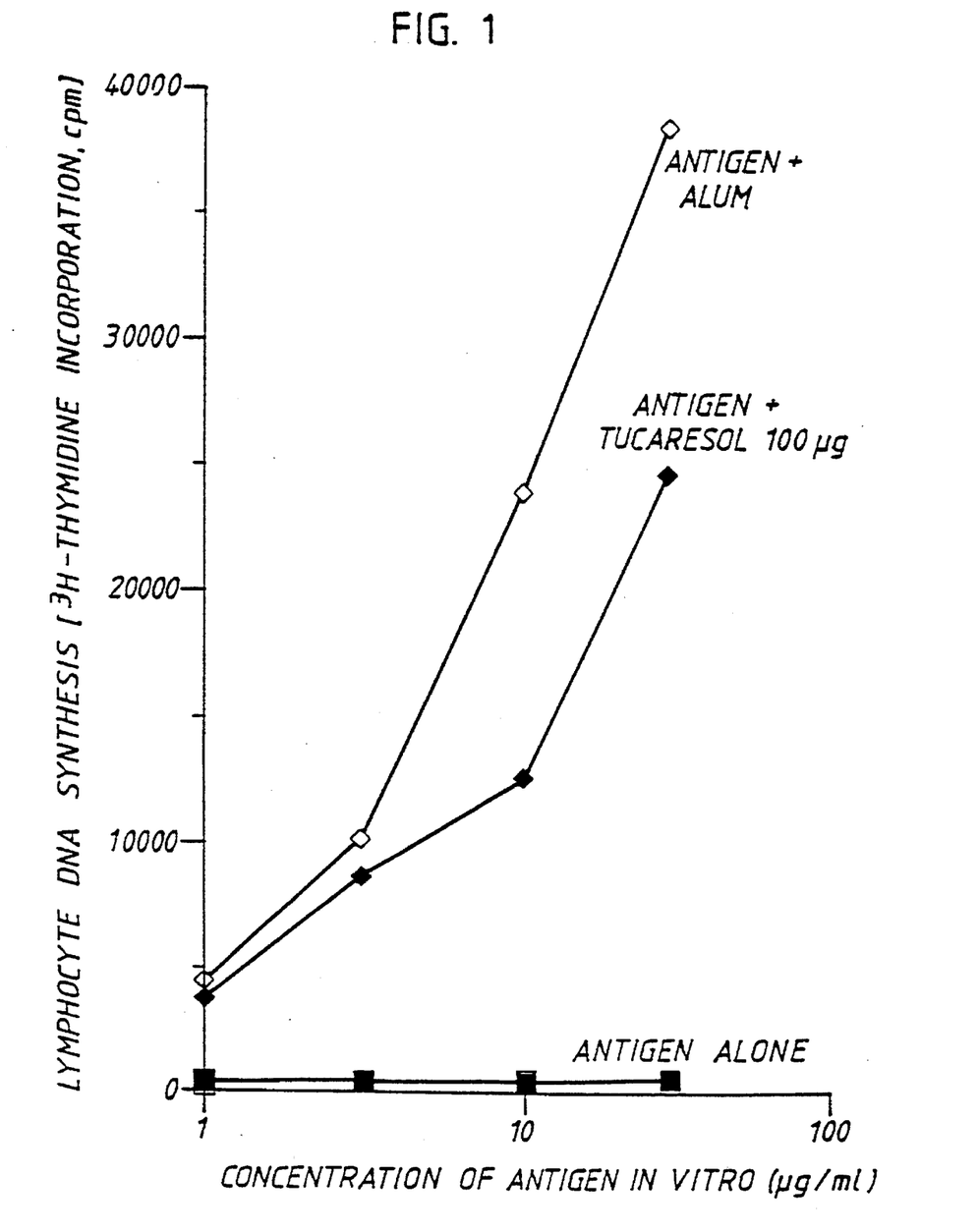
FIG. 1 shows data that shows the effects of tucaresol on T-lymphocyte priming to antigen (keyhole limpet haemocyanin).

The data in FIG. 1 show the effects of the tucaresol on T-lymphocyte priming to antigen (keyhole limpet haemocyanin). B10S mice received 50 μg of antigen either alone (■), with the conventional adjuvant alum (◇), or with 100 μg of Tucaresol (♦).

Figure 2:
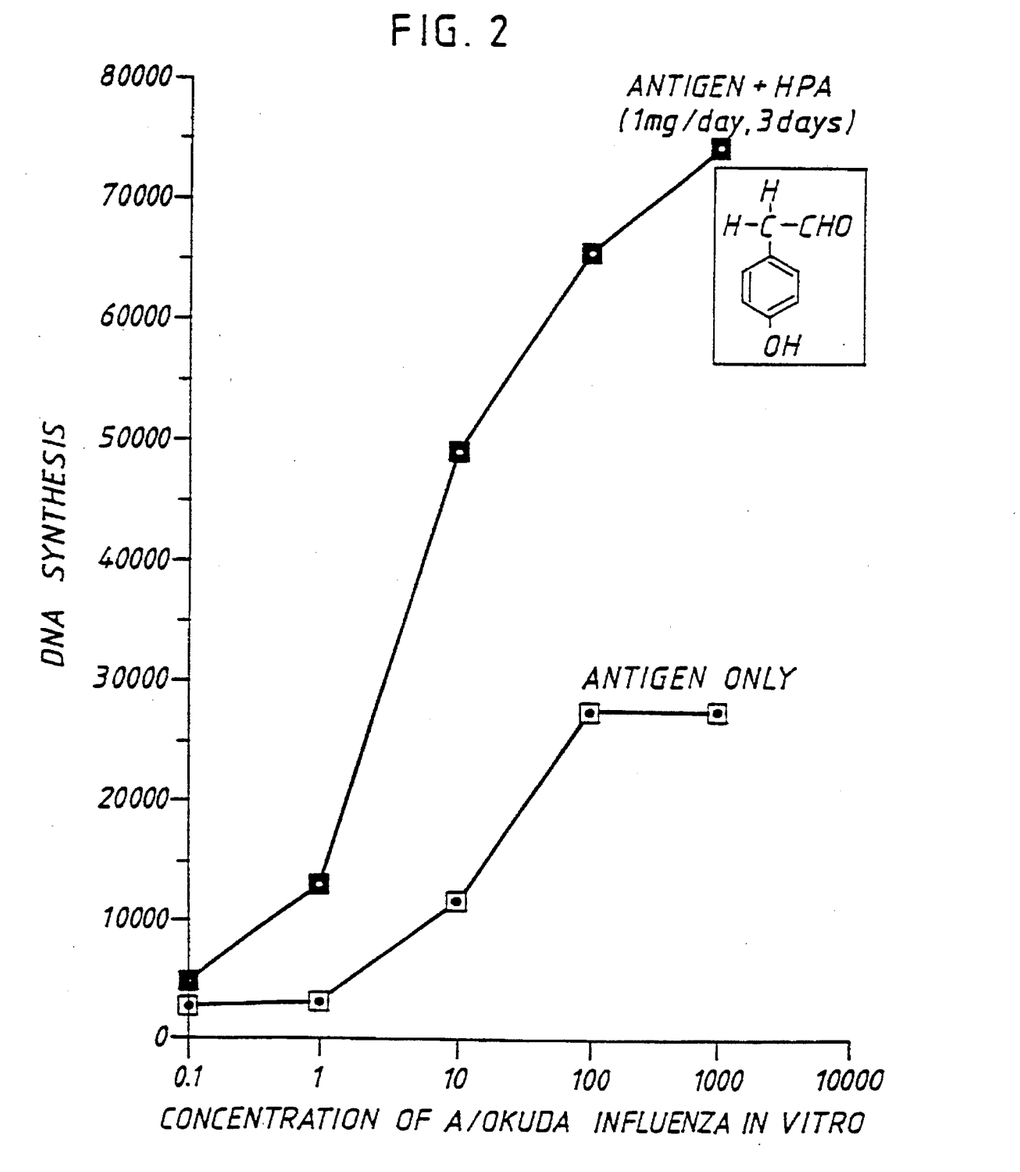
FIG. 2 shows data that shows the effects of the compound p-hydroxypenylacetaldehyde on T-cell priming to recombinant nucleprotein of influenza virus B1OS mice.

The data in FIG. 2 show the effects of the small Schiff base-forming compound p-hydroxyphenylacetaldehyde (pHPA) (compound 1) on T-cell priming to recombinant nucleoprotein (NP) of influenza virus in B10S mice. On day 0 mice received 1 μg of NP either alone (□) or with ling of pHP A (■). The pHPA group received a further injection of ling of pHPA on days 1 and 2 three injections in all). After 7 days regional lymph nodes were removed and the lymph node cells restimulated with A/Okuda influenza virus. Antigen specific proliferation was measured after a further 4 days as described.

Figure 3:
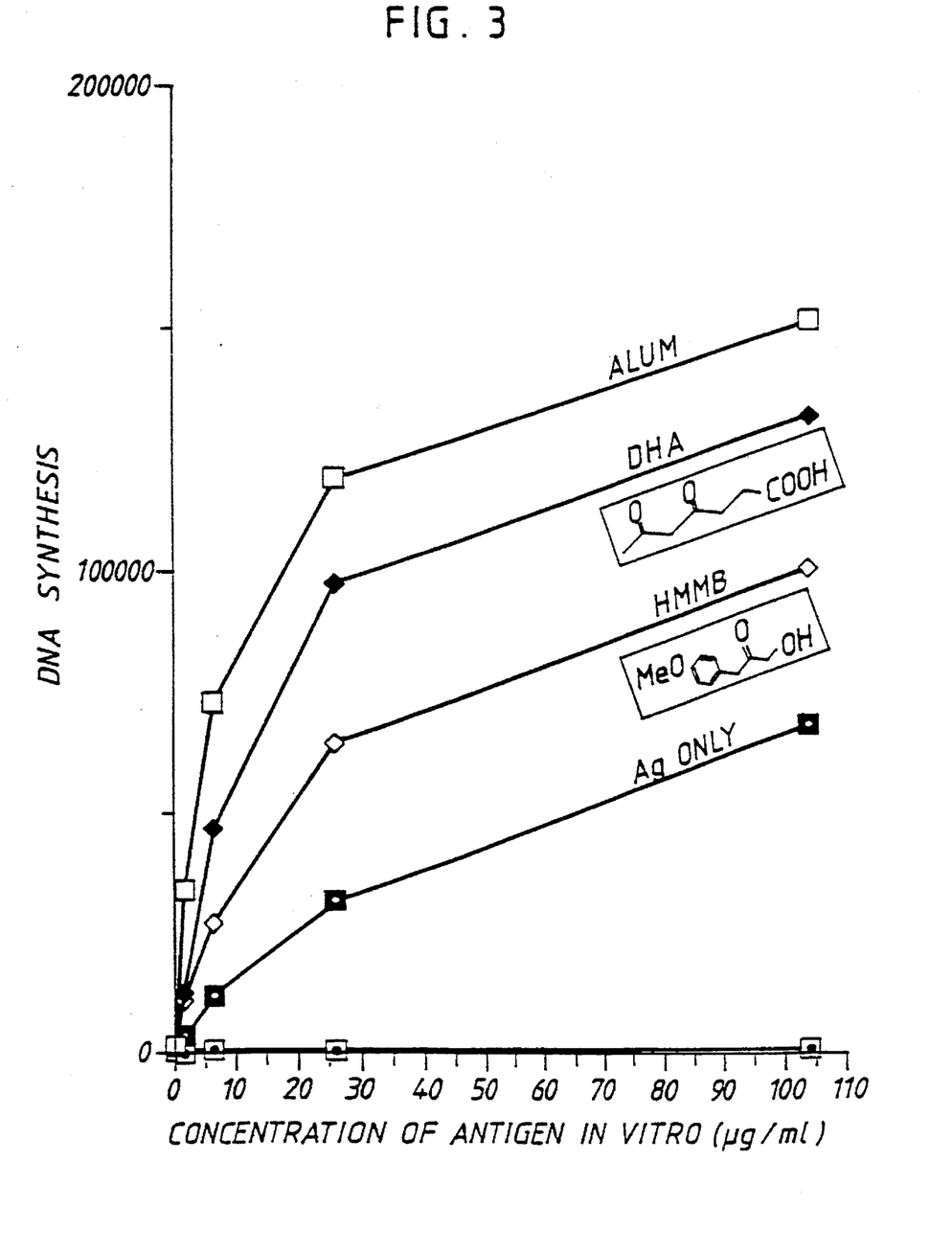
FIG. 3 shows data that shows the effects of dioxptanoic acid and 3-hydroxy-1-(4-methoxyphenyl)-3-methyl-2-butanone on the response to keyhole limpet haemocyanin in B10 mice.

The data in FIG. 3 show the effects of the Schiff base-forming ketones dioxoheptanoic acid (DHA) (compound 12) and 3-hydroxy-1-(4-methoxyphenyl)-3-methyl-2-butanone (HMMB) (compound 18) on the response to keyhole limpet haemocyanin (KLH)in B10S mice. A single injection of KLH (10 μg) was given on day 0 and test compounds were administered at the same site on days 0, 1, 2 and 3. After 7 days regional lymph nodes were removed and LNC restimulated with antigen to measure T-cell priming in the standard procedure. Test compounds were compared with the conventional adjuvant aluminium hydroxide (100 μg mixed with the antigen) as follows. Antigen alone (■). Antigen plus alum (□). Antigen plus DHA 1 mg (♦). Antigen plus HMMB 2 mg (◇).

Figure 4:
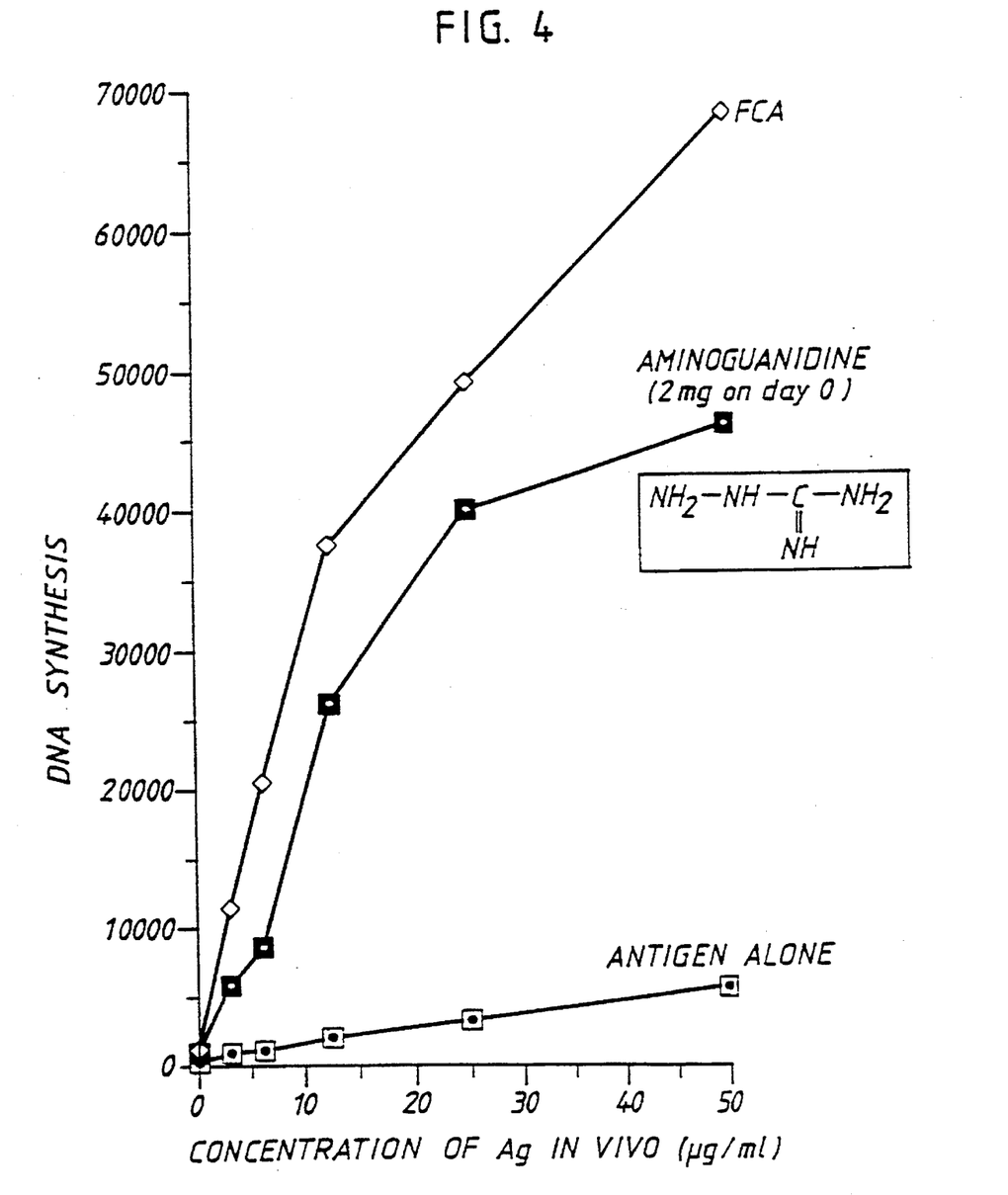
FIG. 4 shows data that shows the effects of aminoguanidine on T-cell responsiveness.

The data in FIG. 4 show the effects of aminoguanidine, on T-cell responsiveness. This compound is a nucleophilic hydrazine which reacts readily with cellular carbonyl groups to form carbonyl-amino condensations. (The bond formed is a hydrazone, similar to a Schiff base but more stable). Mice received a single injection of KLH (50 μg) either alone (●), emulsified with Freunds complete adjuvant (◇), or with 2 mg of aminoguanidine (■). T-cell priming in regional lymph nodes was assessed by the standard procedure.

Figure 5:
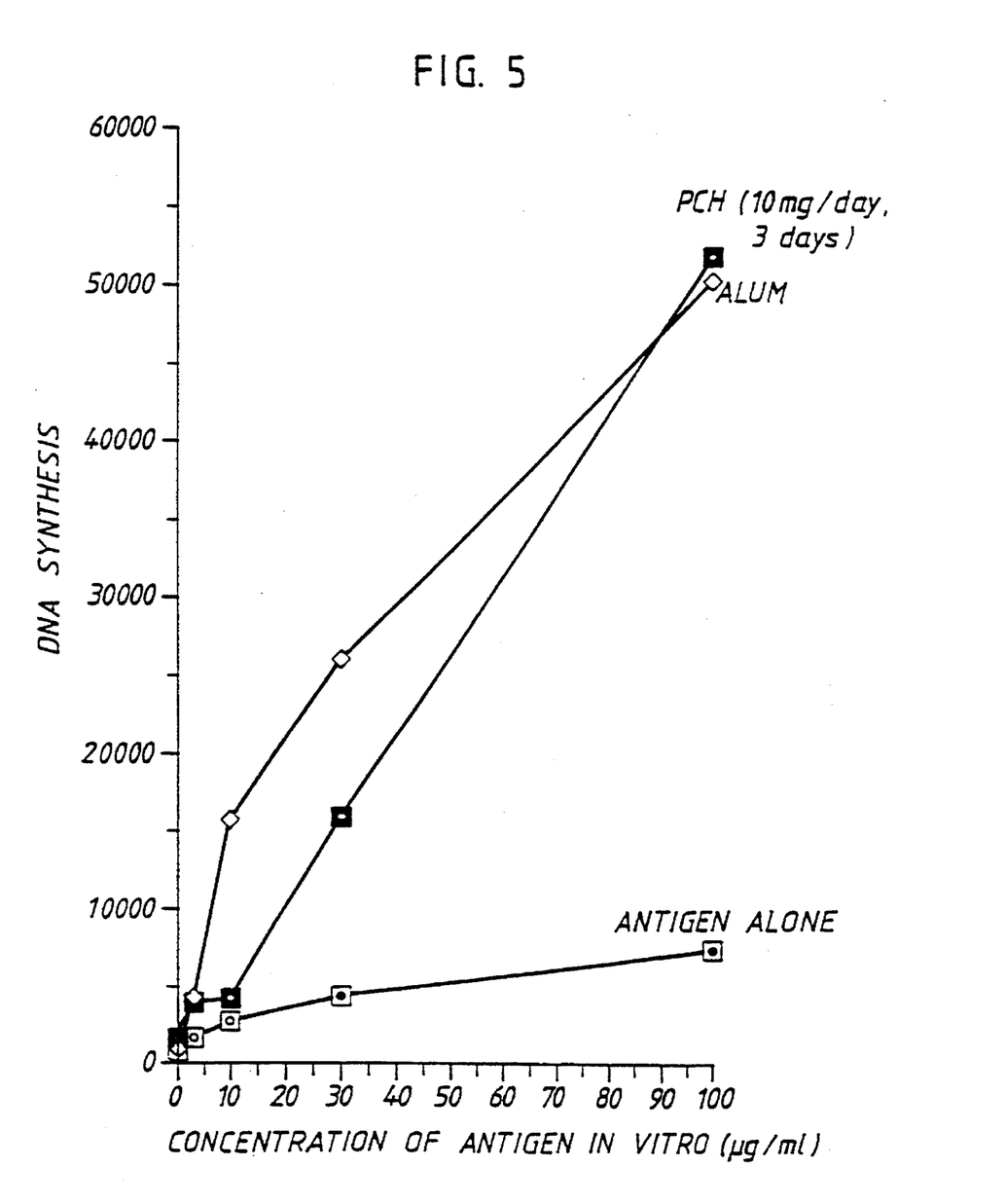
FIG. 5 shows data that shows the effects of pyridinium chloride hydrazide on T-cell responsiveness.

The date in FIG. 5 show the effects of the hydrazone forming molecule pyridinium chloride hydrazide on T-cell responsiveness. Mice received a single injection of antigen (50 μg of ovalbumin) either alone (□), with 100 μg of alum (◇), or with 10 mg of PCH followed by two more daily doses of 10 mg PCH at the same site (■). T-cell priming was assessed by the standard procedure.

Figure 6:
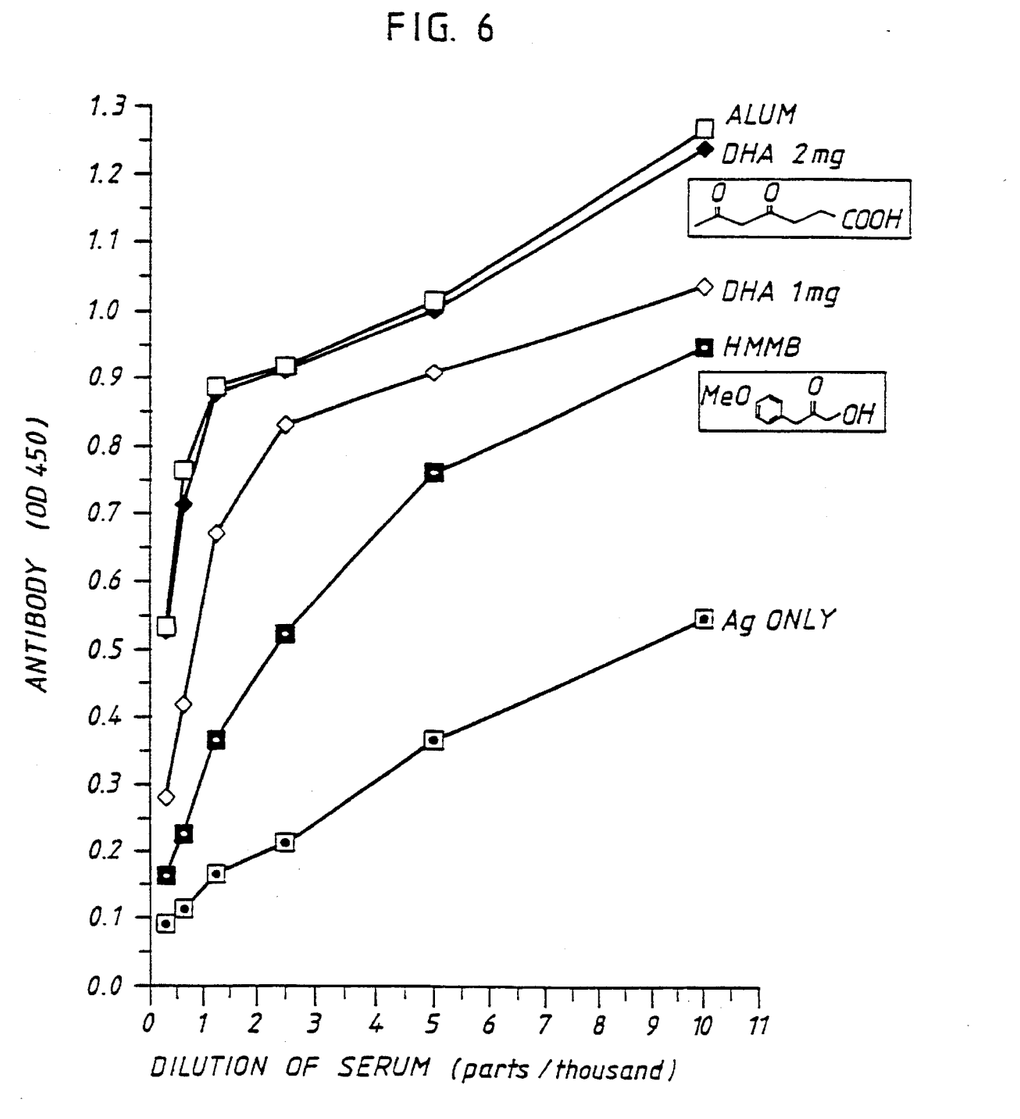
FIG. 6 shows data that shows the effects of dioxheptanoic acid and 3-hydroxy-1-(4-methoxyphenyl)-3-methyl-2-butanone on the primary antibody response to antigen (10 μg of ovalbumin) in comparison with the adjuvant alum.

The data in FIG. 6 show the effects of the Schiff base forming compounds DHA and HMMB on the primary antibody response to antigen (10 μg of ovalbumin) in comparison with the standard physico-chemical adjuvant alum. Antigen alone (□). Antigen plus alum (□). Antigen plus 2 mg DHA (♦). Antigen plus ling DHA (◇), antigen plus 2 mg HMMB (■).

Figure 7:
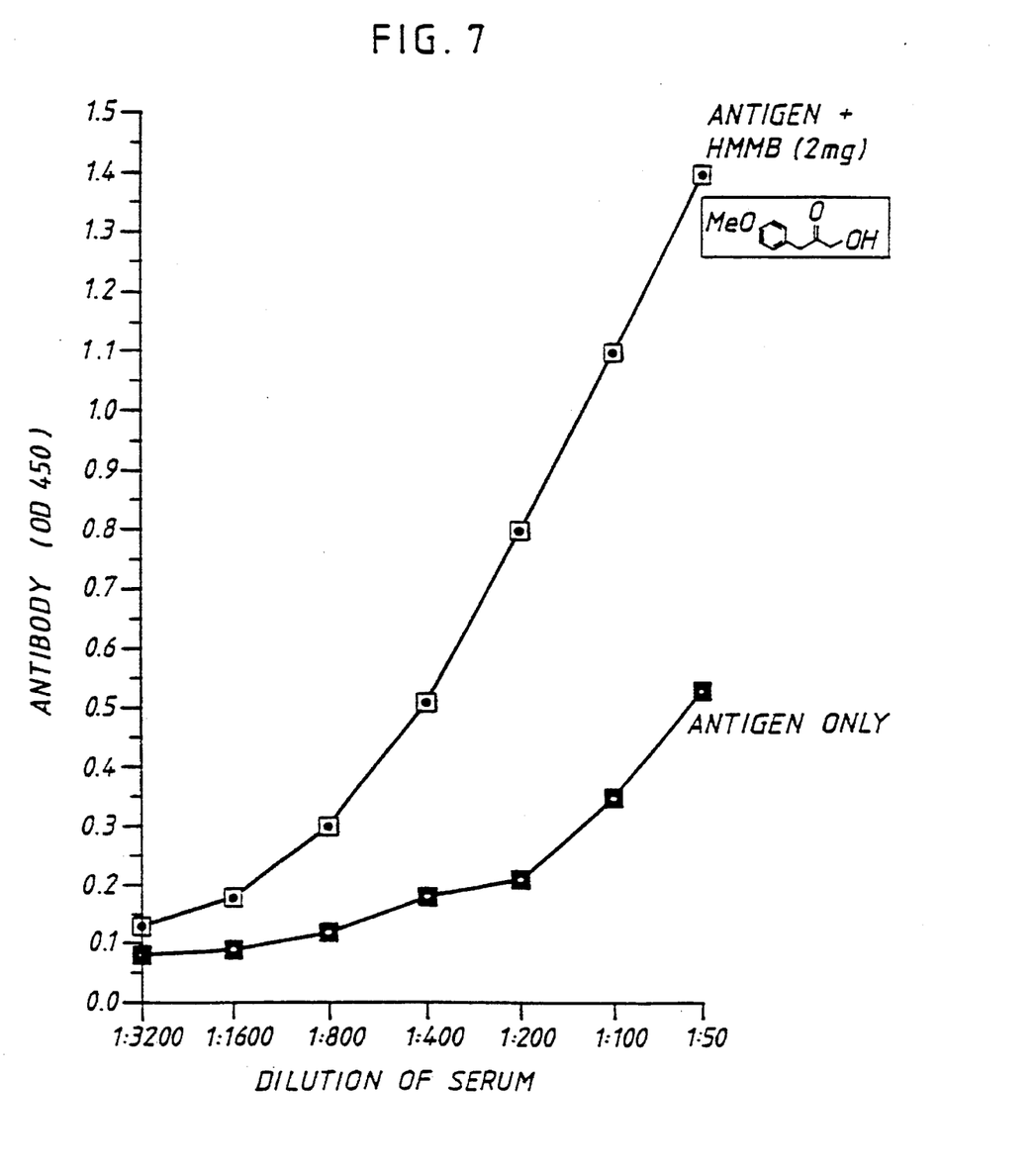
FIG. 7 shows data that shows the effects of 3-hydroxy-1-(4-methoxyphenyl)-3-methyl-2-butannone on the primary antibody response to keyhole limpet haemocyanin in B1OS mice.

The data in FIG. 7 show the effects of HMMB on the primary antibody response to KLH in B10S mice. Mice received 10 μg of antigen alone (■), or antigen plus 2 mg HMMB (●).

The above results show that small compounds capable of forming carbonyl-amino condensations (either Schiff bases or hydrazones) with cell-surface groups are potent enhancers of immune responses in mice.

EXAMPLE 2

Antitumour Activity of Tucaresol

The activity of the tucaresol was evaluated against the outgrowth of subcutaneously implanted mouse colon adenocarcinoma 38 (MCA38) in female C57BL/6 mice, using the following protocol:

| Day 0 | Fifteen, female and 16 male C57BL/6 mice each implanted subcutaneously with one 2 mm cube of tumour. Mice randomized and divided into three groups - Group A, 5 females and 5 males, Group B, 5 females and 5 males, Group C, 5 females and 6 males. |
| Day 5 to Day 22 | Test groups B and C each dosed with 589C80 (1 mg or 0.2 mg per mouse dissolved in 0.2 ml PBS, intraperitoneally) once every alternate day (total of 9 doses). Control mice (group A) given PBS alone. |
| Day 24 | All mice killed, tumours excised and weighed. Mean and median tumour weight in test group compared with that in controls. |

Tucaresol was dissolved in PBS by dropwise addition of 1M KOH to pH 10.0 followed by dropwise addition of conc. HCL to return pH to neutral.

Dosing schedule where drug was given on alternate days was chosen in order to extend the dosing period over 14 rather than 7 days. By so doing tumours were exposed to the drug from day 13 right up until day 25 i.e. 2 days before the experiment was terminated. Results are shown in Table 1.

The pattern of tumour growth (diffuse granular) rendered calliper measurements of volume, meaningless and such data are therefore not included.

TABLE 1

TUMOUR WEIGHT (grammes)
ON DAY 24 AFTER TUMOUR IMPLANTATION

|  | GROUP A controls | GROUP B, 1.0 mg/mouse | GROUP C, 0.2 mg/mouse |
| --- | --- | --- | --- |
|  | 1.207 | 0.740 | 0.802 |
|  | 1.130 | 0.695 | 0.272 |
|  | 0.772 | 0.358 | 0.230 |
|  | 0.728 | 0.303 | 0.197 |
|  | 0.636 | 0.298 | 0.181 |
|  | 0.575 | 0.090 | 0.126 |
|  | 0.335 | 0.079 | 0.126 |
|  | 0.276 | 0.038 | 0.085 |
|  | 0.060 | 0.022 | 0.029 |
|  | N.T. | N.T. | 0.019 |
|  |  |  | 0.006 |
| Mean | 0.635 | 0.291 | 0.188 |
| S.D. | 0.379 | 0.272 | 0.222 |
| Mean % red. | — | 54.2 | 70.4 |
| Median | 0.636 | 0.298 | 0.126 |
| Median % red. | — | 53.15 | 80.19 |

N.T. — no tumour take. These mice not included in derived values given above.
Tucaresol inhibited the outgrowth of subcutaneously implanted MCA38 in syngeneic C57BL/6 mice.

Experimental protocol for results in Table 2

Blood from healthy donors who had been immunised within the last five years with tetanus toxoid was taken by venipuncture. The mononuclear cell fraction was prepared by density gradient centrifugation on Ficoll triosil (Lymphoprep, Nycomed AS Oslo, Norway). Cells were washed and resuspended in RPMI 1640 tissue culture medium (Flow Laboratories, Ayrshire, Scotland) containing 10% autologous serum and supplemented with antibiotics. Cells were adjusted to $10^6$ per ml and 100 μl aliquots were placed in each well of 96-well tissue culture microtitre plates (u-shaped wells) (Titertek, Flow Labs). Test compounds were added in 10 μl volumes to each well and suitable vehicle controls were also added at this stage. Affinity purified tetanus toxoid was added at a final concentration of 10 μg per ml. The cells were cultured for five days in humidified air containing 5% $CO_2$ at 37° C. with $^3H$ thymidine present for the last 18 hours of culture (1 μCi per well). Cells were harvested onto glass microfibre paper by a semi-automatic system (Skatron) and the degree of thymidine incorporation into DNA was determined by liquid scintillation spectrometry. IC50 ratios were determined in comparison with the benchmark compound p-hydroxyphenylacetaldehyde The mechanism by which Schiff base forming compounds influence immune responses either positively or negatively is the same in that compounds react with amino groups on the surface of lymphocytes and antigen presenting cells (APC). In this way they provide costimulation to T-cells, amplifying the costimulation provided by physiological Schiff base-formation between ligands on the surface of cells. At high concentrations, however, the compounds will pre-empt the reaction between cellular ligands which, in addition to providing costimulation, appears to be necessary for the effective binding of APC to T-cell. Low and intermediate concentrations will thus enhance immune responses whereas high concentrations will be inhibitory. The inhibitory effect occurs more readily in vitro (because processed antigen on the surface of APC is a limiting element) and provides a measure of Schiff base forming capacity that reflects immunopotentiating capacity in vivo. Reversibility of Schiff base formation, isomerisations and cycles of protonation and deprotonation may also be important in immunopotentiation, producing deviation from the simple equation of immunosuppression in vitro with immunopotentiation in vivo. In vivo potency will also be influenced by half-life, solubility, and pharmacokinetic properties of compounds.

TABLE 2

IMMUNOSUPPRESSION IN VITRO BY SCHIFF BASE FORMING COMPOUNDS

| Compound Name | Structure | IC50 Ratio with 4-Hydroxyphenyl-acetaldehyde |
|---|---|---|
| 1. 4-Hydroxyphenyl-acetaldehyde | HO-C$_6$H$_4$-CH$_2$CHO | 1 |
| 2. Phenylacetaldehyde | C$_6$H$_5$-CH$_2$CHO | 10 |
| 3. 4-Methoxyphenyl acetaldehyde | CH$_3$O-C$_6$H$_4$-CH$_2$-CHO | 1.4, 1.9, 1.9, 2.3 |
| 4. Sodium 1-hydroxy-2-phenylpropane sulphonate tested as the aldehyde | CH$_3$-CH(C$_6$H$_5$)-CHO | 30, >30 |
| 5. 3-Phenylproponion-aldehyde | CH$_3$-CH(C$_6$H$_5$)-CHO | 40 |
| 6. 4-Nitrobenzaldehyde | O$_2$N-C$_6$H$_4$-CHO | 7 |
| 7. Methyl 4-formylbenzoate | OHC-C$_6$H$_4$-CO$_2$Me | 8.5 |
| 8. 4-Chlorobenzaldehyde | Cl-C$_6$H$_4$-CHO | >4 |
| 9. 4-Methoxybenzaldehyde | MeO-C$_6$H$_4$-CHO | >4, >10 |
| 10. 4-Methylbenzaldehyde | Me-C$_6$H$_4$-CHO | >5, >20 |
| 11. 8,10-Dioxoundecanoic acid | CH$_3$-CO-CH=C(OH)-(CH$_2$)$_5$-CO$_2$H | 50 |

TABLE 2-continued

IMMUNOSUPPRESSION IN VITRO BY SCHIFF BASE FORMING COMPOUNDS

| Compound Name | Structure | IC50 Ratio with 4-Hydroxyphenyl-acetaldehyde |
|---|---|---|
| 12. 4,6-Dioxoheptanoic acid | | 80 |
| 13. Pentanedione | | 8 |
| 14. 5-methoxy-1-tetralone | | 11 |
| 15. 6-methoxy-1-tetralone | | 11 |
| 16. 7.methoxy-1-tetralone | | 16 |
| 17. 2-tetralone | | 2, 1 |
| 18. 3-hydroxy-1-(4-methoxyphenyl)-3-methyl-2-butanone | | 0, 34, 2.0, 1.0 |
| 19. 2α,4'-dihydroxy-2-(4-methoxyphenyl)acetophenone | | 2.7 |
| 20. 2-hydroxy-1-(4-methoxyphenyl)-pent-2ene-4one | | 4, 6.6 |
| 21. Naringenin 4',5,6-trihydroxyflavonone | | 1, 5 |

TABLE 2-continued

IMMUNOSUPPRESSION IN VITRO BY SCHIFF BASE FORMING COMPOUNDS

| Compound Name | Structure | IC50 Ratio with 4-Hydroxyphenyl-acetaldehyde |
|---|---|---|
| 22. 4'-methoxy-2-(4-methoxyphenyl)acetophenone | | 5.5 |
| 23. 6,7-dihydroxycoumarin | | 2.3 |
| 24. 7-methoxy-2-tetralone | | 3.0 |
| 25. 6,7-dimethoxy-2-tetralone | | 2.7 |
| 26. 6-hydroxy-4-methylcoumarin | | 2, 2.5 |
| 27. Homogentisic acid gamma lactone | | .25, 0.5, 0.7, 1.5 |
| 28. 6-hydroxy-1,2-naphthoquinone | | 0.2, 0.5, 1.0 |
| 29. 8-methoxy-2-tetralone | | 0.8, 1.0 |

I claim:

1. A method for treating an immunodeficient mammal which comprises administering to the mammal an effective amount of a compound of formula (I)

$$B^1\text{—N} \qquad (I)$$

which forms a Schiff base with T-cell surface carbonyl groups, for the potentiation of an immune response, wherein N is hydrogen or n is 0 or 1;
B is hydrogen or $C_{1-4}$alkyl;
$B^1$ is optionally substituted phenyl;

$B^2$ is methyl or may be linked to $B^1$ when $B^1$ is phenyl to form a optionally substituted bicyclic ring system containing 8 or 10 atoms of which one may be oxygen and the rest carbon, or when n is 1, $B^1$ is hydrogen and $B_2$ is $CH_2CO(CH_2)_xCOOH$ wherein x is 1 to 7, with the proviso that the compounds coumarin, cinnaldehyde and 4-(2-formyl-3-hydroxyphenoxymethyl)benzoic acid excluded.

2. A method according to claim 1 wherein the group of compounds of formula (I) is where N is hydrogen and $B^1$ is represented by formula (II)

(II)

wherein $Y^1$ is selected from hydrogen, hydroxy, $C_{1-4}$ alkylamino, and alkanoylamino having 1 to 4 carbon atoms in the alkyl moiety thereof;

$Y^2$, $Y^3$ and $Y^4$ and are independently selected from hydrogen, halogen, $C_{1-4}$ alkyl, $C_{1-4}$ alkoxy, trifluoromethyl, hydroxyl and benzyloxy; and $Y^5$ is hydroxyl or a group $Q^1$ wherein $Q^1$ is either where $Q^2$ and $Q^3$ are independently selected from hydrogen and $C_{1-4}$ alkyl;

X is selected from cyano, carboxyl or a derivative thereof, 5-tetrazolyl and alkylsulphonylcarbamoyl having 1 to 6 carbon atoms in the alkyl moiety thereof; and n is 0 to 6.

$Y^6$ is $—(C_pH_{2p})CHO$, wherein p=0 to 5 when p is >1 the formyl(—CHO) group may be on any carbon atom and the alkylene $(C_pH_{2p})$ may be linear or branched;

or $Y^6$ is $(CH_2CO)_q—X^1$ or $(COCH_2)_q—X^1$ where q=1 to 3 and $X^1$ is methoxyphenyl, or $C_{1-4}$ alkyl and physiologically acceptable salts thereof.

3. A method according to claim 1 wherein

X is selected from cyano, 5-tetrazolyl, alkylsulphonylcarbamoyl having 1 to 6 carbon atoms in the alkyl moiety thereof and a group —CO.Y, where Y is —$OR^1$ and $R^1$ is hydrogen, alkyl of 1 to 4 carbon atoms or benzyl, or Y is —$NR^2R^3$ where $R^2$ and $R^3$ are independently hydrogen or alkyl of 1 to 4 carbon atoms, and physiologically acceptable salts thereof.

4. A method according to claims 1 or 2 wherein X is carboxyl, together with physiologically acceptable salts thereof.

5. Method according to claim 1 wherein $B_1$ and $B_2$ form a bicyclic ring system which is selected from tetralone, substituted by up to four substituents selected from hydrogen, $C_{1-4}$ alkoxy, hydroxy or hydroxy substituted phenyl.

6. The method of claim 1 in which the compound is 4-hydroxyphenyl acetaldehyde.

* * * * *